United States Patent [19]

Reckwerdt et al.

[11] Patent Number: 5,673,300
[45] Date of Patent: Sep. 30, 1997

[54] METHOD OF REGISTERING A RADIATION TREATMENT PLAN TO A PATIENT

[75] Inventors: Paul J. Reckwerdt; Thomas R. Mackie, both of Madison, Wis.

[73] Assignee: Wisconsin Alumni Research Foundation, Madison, Wis.

[21] Appl. No.: 661,538

[22] Filed: Jun. 11, 1996

[51] Int. Cl.⁶ .................................................. A61N 5/10
[52] U.S. Cl. ....................................... 378/65; 378/8
[58] Field of Search ................................. 378/8, 65, 94, 378/20, 95

[56] References Cited

U.S. PATENT DOCUMENTS 4,858,128  8/1989  Nowak ........................ 364/413.13
5,457,724  10/1995  Toth ................................... 378/4
5,538,494  7/1996  Matsuda ............................ 600/1
5,586,201  12/1996  Whiting et al. ................. 378/98.2

Primary Examiner—David P. Porta
Assistant Examiner—David Vernon Bruce
Attorney, Agent, or Firm—Quarles & Brady

[57] ABSTRACT

A method for aligning a patient for radiation treatment based on an earlier tomographic scan of the patient uses projection images used to reconstruct a tomographic image rather than reconstructed images and compares the projection images directly to projection images taken at the time of the radiation therapy to determine a series of offsets of the patient which may be used to characterize and correct for motion of the patient between the initial tomographic scan, used for treatment planning, and one or a series of subsequent radiation treatment sessions.

12 Claims, 4 Drawing Sheets

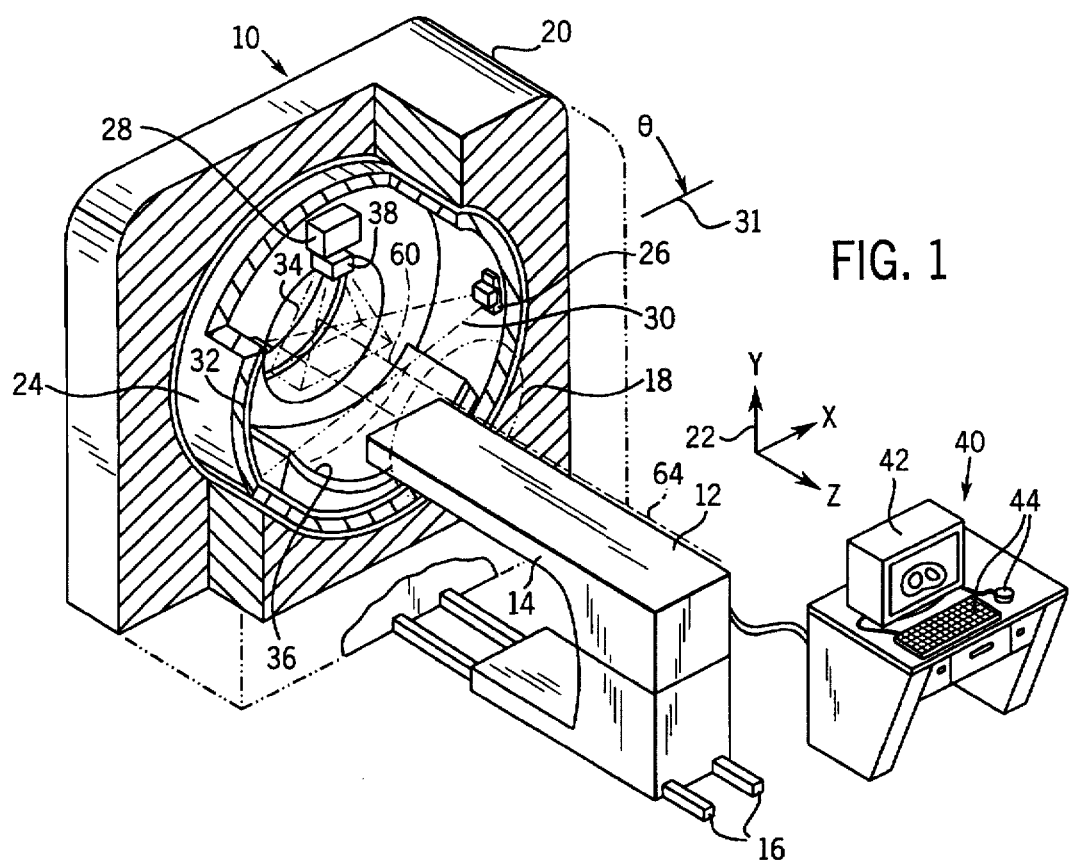
FIG. 1
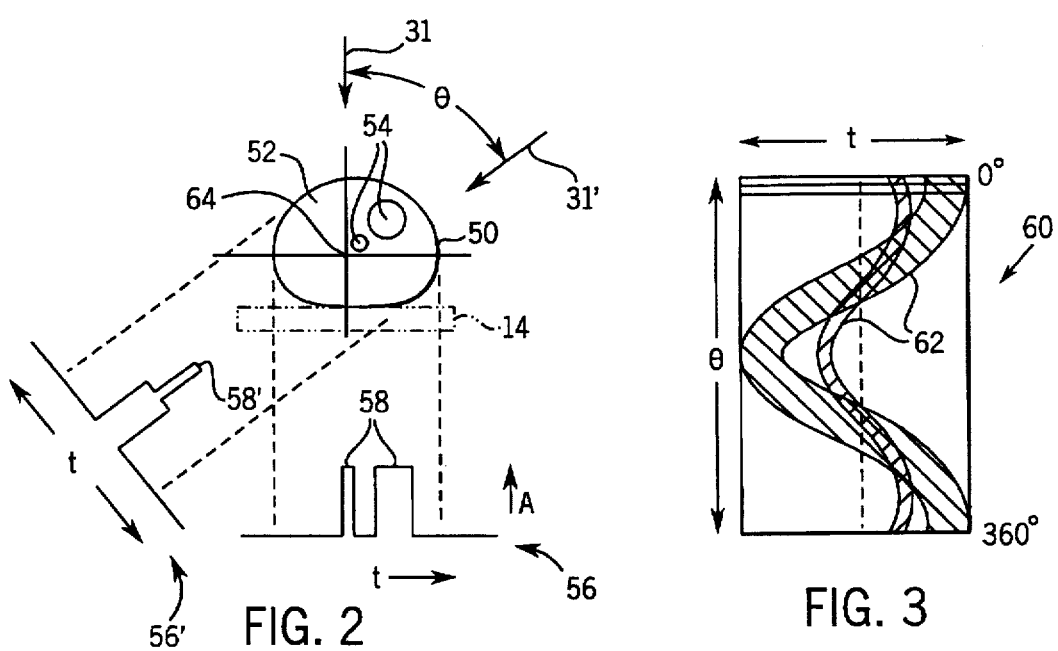
FIG. 2
FIG. 3

METHOD OF REGISTERING A RADIATION TREATMENT PLAN TO A PATIENT

FIELD OF THE INVENTION

This invention relates generally to radiation therapy equipment for the treatment of tumors, or the like, and specifically to a computerized method for aligning a patient with a previously prepared radiation treatment plan.

BACKGROUND OF THE INVENTION

Medical equipment for radiation therapy treats tumorous tissue with high energy radiation. The amount of radiation and its placement must be accurately controlled to ensure both that the tumor receives sufficient radiation to be destroyed, and that the damage to the surrounding and adjacent non-tumorous tissue is minimized.

In external source radiation therapy, a radiation source external to the patient treats internal tumors. The external source is normally collimated to direct a beam only to the tumorous site. The source of high energy radiation may be x-rays, or electrons from linear accelerators in the range of 2–25 MeV, or gamma rays from highly focused radioisotopes such as a $Co^{60}$ source having an energy of 1.25 MeV.

Typically the tumor will be treated from several different angles with the intensity and shape of the beam adjusted appropriately. The purpose of using multiple beams, which converge on the site of the tumor, is to reduce the dose to areas of surrounding non-tumorous tissue. The angles at which the tumor is irradiated are selected to avoid angles which would result in irradiation of particularly sensitive structures near the tumor site. The angles and intensities of the beams for a particular tumor form a treatment plan for that tumor.

One highly accurate method of controlling the dose to a patient employs a radiation source that produces a fan beam composed of many individual rays whose intensity may be independently controlled. The fan beam orbits the patient within a plane illuminating a slice of the patient, while the intensity of each ray of the fan beam is modulated as a function of that angle. By properly selecting the beam intensities at different angles, complex regions within the slice may be accurately irradiated. U.S. Pat. 5,317,616, issued May 31, 1994 and assigned to the same assignee as the present application, describes the construction of one such machine and one method of calculating the necessary beam intensities as a function of angle.

In order to take advantage of the improved accuracy in dose placement offered by such radiation therapy systems, the radiation treatment plan may be based on a computed tomography ("CT") image of the patient. As is known in the art, a CT image is produced by a mathematical reconstruction of many projection images obtained at different angles about the patient. In a typical fan beam CT acquisition, the projections are one-dimensional line images indicating the attenuation of the fan beam by a "slice" of the patient. After reconstruction of the two-dimensional tomographic image of the slice, the projection data, which by itself is unintelligible, is no longer used or accessed by the user.

Using the CT image, the radiologist views the tumorous area and determines the beam angles and intensities (identified with respect to the tumor image) which will be used to treat the tumor. In an automated system, a computer program selects the beam angles and intensities after the physician identifies the tumorous region and upper and lower dose limits for the treatment.

Normally, the CT image of the patient is acquired substantially before the radiation treatment to allow time for the treatment plan to be prepared. As a result, the patient will have moved in position in between the time of the CT image acquisition and the radiation treatment. This will also be true in cases where the treatment occurs during a number of different treatment sessions over time.

Uncertainty in the positioning of the patient with respect to the original CT image can defeat much of the accuracy gains expected from the use of a CT image for treatment planning.

SUMMARY OF THE INVENTION

The present invention provides a method of correcting for patient misalignment between the time of a planning CT image and radiotherapy by comparing one or more radiographic projections taken of the patient immediately prior to the radiotherapy to selected ones of the projections underlying the planning CT image. By using the raw projection data from the CT image, rather than the reconstructed image itself, the comparison can be made rapidly and without additional time consuming tomographic reconstructions. Linear displacements, rotations and twisting of the patient (henceforth collectively termed "movement"), all may be detected and compensated for either by modifying the radiation treatment plan or repositioning the patient.

Specifically, the method obtains a planning tomographic projection set of the treatment volume in the patient. A later confirmation projection set of the treatment volume is also obtained of the patient having a second position. An electronic computer produces a radiation treatment plan from the planning tomographic projection set, the treatment plan describing at least one orientation of a radiation beam with respect to the patient which provides a desired treatment of the patient. The computer also receives the confirmation projection set (typically at a later time) then compares radiographic projections from the planning tomographic projection set to radiographic projections from the confirmation projection set to determine a displacement of the patient between the first position and the second position. The treatment of the patient is then changed according to the displacement determined by the electronic computer. The comparison of projections may be a simple correlation between projections along given axis.

Thus, it is one object of the invention to provide a method of accurately registering a previously prepared treatment plan with a patient at the time of radiation treatment, where the method makes direct use of radiographic projections rather than a reconstruction of volumes from those projections, the latter of which would interpose additional delay in the treatment process.

It is another object of the invention to limit the need, at the time of radiation therapy, to obtain full tomographic projection sets of the patient such as would be necessary to compare tomographic images. The ability to directly compare projection data allows a limited number of projections to be taken of the patient. For example, a single projection along each of the x, y and z-axis may accurately determine an x, y and z offset.

It is another object of the invention to provide a registration method which can accommodate complex combinations of rotation, translation and twisting of the patient. The projections compared between the planning and confirmation projection set may be single projection lines obtained by a fan beam. Multiple comparison of multiple lines provide a series of different offsets which may be analyzed as a whole to detect complex changes in the patient position.

The foregoing and other objects and advantages of the invention will appear from the following description. In the description references made to the accompanying drawings which form a part hereof and in which there is shown by way of illustration, the preferred embodiment of the invention. Such embodiment does not necessarily represent the full scope of the invention, however, and reference must be made therefore to the claims herein for interpreting the scope of the invention.

BRIEF DESCRIPTION OF THE DRAWINGS

FIG. 1 is a perspective, cut-away view of a radiation therapy system providing for the acquisition of radiographic projections and for the generation of high energy radiation therapy beams and showing a patient table for supporting a patient thereon;

FIG. 2 is a simplified view of a slice of an object, such as a patient, showing line projections of the object taken at two angles q, with attenuations A along dimension t indicated in the vertical axis of each projection;

FIG. 3 is a sinogram formed of multiple line projections such as those acquired in FIG. 2, over 360 degrees of angle q with the attenuation of the projections indicated by shading;

DETAILED DESCRIPTION OF A PREFERRED EMBODIMENT

Figure 4:
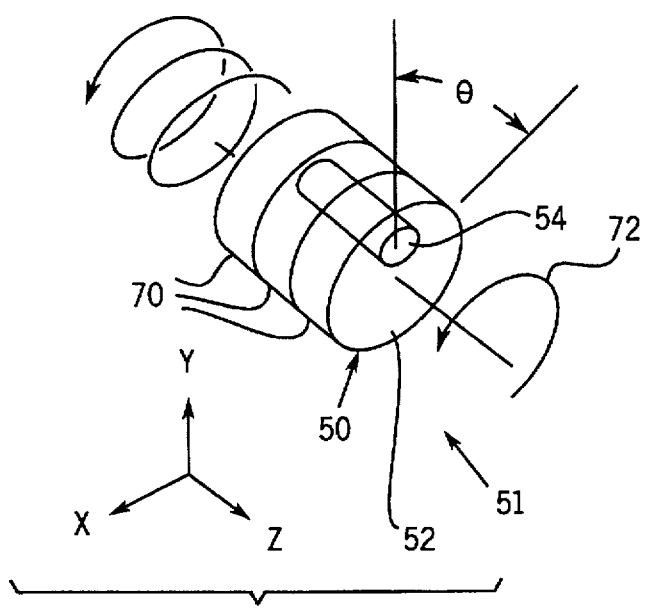
FIG. 4 is a perspective view of a simplified object that may be scanned showing a helical and slice-by-slice scanning path.

Referring now to FIG. 1, a radiation therapy machine 10, suitable for use with the present invention, includes a radiotranslucent table 12 having a cantilevered top 14. The table top 14 is received within a bore 18 of an annular housing 20 of the machine 10 with movement of the table 12 along tracks 16 extending along a z-axis of a Cartesian coordinate system 22.

Table 12 also includes an internal track assembly and elevator (not shown) to allow adjustment of the top 14 in a lateral horizontal position (indicated by the x-axis of the coordinate system 22) and vertically (indicated by the y axis of the coordinate system 22). Motion in the x and y directions are limited by the diameter of the bore 18.

A rotating gantry 24, coaxial with the bore 18 and positioned within the housing 20, supports an x-ray source 26 and a high energy radiation source 28 on its inner surface. The x-ray source 26 and a radiation source 28 rotate with the gantry 24 about a center of rotation 64 near the top of patient table 12 when the table top 14 is positioned within the bore 18.

The x-ray source 26 is collimated to produce a fan beam 30 lying generally within the x-y plane and crossing the bore 18 and thus the table top 14 when table top 14 is positioned within the bore 18. The fan beam 30 diverges about a central axis 31 whose angle is controlled by the position of the gantry 24. The axis 31 will henceforth be termed the projection axis.

After exiting the table top 14, the fan beam 30 is received by a linear array detector 32 positioned diametrically across from the radiation source 28. Thus, the rotating gantry 24 permits fan beam radiographic projections of a patient on the table top 14 to be acquired at a variety of angles q about the patient.

The radiation source 28 is mounted so as to project a fan beam of high energy radiation 34, similar to the fan beam 30, but crossing fan beam 30 at right angles so as to be received on the other side of the gantry 24 by radiation detector and stop 36. The fan beam of high energy radiation 34 diverges about a radiation axis centered within the beam and perpendicular to the projection axis 31.

The radiation source 28 has a collimator 38 mounted in front of it to divide the fan beam of high energy radiation 34 into multiple adjacent rays whose intensity may be individually controlled. A collimator of this type is described in U.S. Pat. 5,317,616 assigned to the assignee of the present case and hereby incorporated by reference. The location of the radiation source 28 and x-ray source 26 are precisely characterized so that images obtained from the radiation source 28 may be used to aim the radiation source 28.

A computer 40 having a display screen 42 and user entry mouse and keyboard 44 well known in the art is connected to the radiotherapy machine 10 to control motion of the table 12 and to coordinate operation of the gantry 24 together with the radiation source 28 and x-ray source 26 and to collect data from the linear array detector 32 during a scan of the patient according to methods well known in the art.

Referring now to FIG. 2, a slice 50 of an imaged object taken along the x-y plane includes a low attenuation material 52 having two inclusions 54 of high attenuating material. Radiation passing along beam axis 31 through the slice 50 (at a vertical or anterior/posterior angle ("AP")) produces a projection 56 which records the attenuation of x-rays passing through to slice 50 along a single line perpendicular to the beam axis 31. The distance along this perpendicular to the projection axis is designated: t. The inclusions 54 may be resolved separately at the vertical angle and hence two attenuation peaks 58 are present in the projection 56.

In contrast at a second projection along a projection axis 31' at an angle q from vertical, the inclusions 54 are aligned so that the projection 56' shows a single attenuation peak 58';

Referring now to FIG. 3, projections at a different angle q over 360 degrees, may be combined to form a sinogram 60 which is stored temporarily in computer 40 as a matrix of data. As depicted, this matrix of data is arranged with each row representing a different angle q and each column a different distance t along the projection. Values of attenuation, stored as numeric values in the computer 40, are shown as shaded curves 62.

As is well understood in the art, a sinogram having t values spanning the largest cross sectional width of an imaged slice 50 and q values over 360 degrees is sufficient to reconstruct a tomographic image of the slice through, for example the method of filtered back projection. Such a collection of projections will be termed a tomographic projection set. The pattern of the sinogram 60 is generally that of superimposed sinusoidal curves 62 (hence the name) each curve 62 having a fundamental period in q of 360 degrees as a result of the apparent movement of inclusions 54 in orbit about a center of gantry rotation 64 as projections are taken at various angles q. Generally, objects toward the axis of rotation 64 of the gantry trace smaller amplitude sine curves whereas inclusions 54 further from the center of rotation 64 trace greater amplitude sine curves. The phase of the sine curves depends generally on the initial position of the inclusion 54 with respect to the first projection at q=0.

In a conventional CT acquisition, the sinogram 60 of FIG. 3 is reconstructed into a tomographic image of the slice 50 and then the sinogram 60 is discarded.

The sinogram representation of FIG. 3 may equally represent a radiation treatment plan in which the values at each location (t,q) in the sinogram 60 represent not an attenuation of x-ray radiation, but the strength of one of the multiple adjacent rays of the fan beam of high energy fan beam 34 transmitted through the patient. As discussed in U.S. Pat. 5,317,616, referred to above, such control of a high intensity radiation beam according to a sinogram 60 may be had by means of collimator 38 under control of the computer 40 (shown in FIG. 1) and can very accurately deposit dose within a patient.

For example, if the inclusions 54 of FIG. 2 were tumors, a radiation treatment plan might well conform generally to curves 62 which would produce beams of high intensity radiation that would intersect at the inclusions 54 at a variety of different angles q to produce a high cumulative dose at the inclusions 54 but low dose elsewhere.

Referring again to FIG. 1, it follows that the tomographic image produced from the sinogram 60 may be employed to establish a radiation treatment plan precisely related to that tomographic image. U.S. Pat. application Ser. No. 08/477,055 filed Jun. 7, 1995, hereby incorporated by reference, describes generally an interactive method for generating a treatment plan in the form of a sinogram 60 based on a tomographic image.

Referring now to FIG. 4, in a "slice-by-slice" acquisition the imaged object 51 is divided into a plurality of slices 70 separated along the z-axis and the acquisition of projections is obtained with the beam axis 31 constrained to a single plane as it rotates about the imaged object 51 indicated generally by arrow 72. At the conclusion of 360 degrees of rotation the object is moved along the z-axis by movement of the table 12 until the next slice is aligned with the beam axis 31.

In an alternative acquisition method, termed "helical scanning", the projection axis follows a helical path through the imaged object 51 in which the table 12 is incremented by a small amount in z with each change in angle q.

In the former slice-by-slice acquisition, a series of sinograms 60' is generated, each one identical to that described with respect to FIG. 3 and typically encompassing 360 degrees of gantry motion. Different slices 70 provide z-axis information about the imaged object 51 as reflected in a sequence of sinogram 60' each of which has a different but constant z value.

In contrast, the helical acquisition produces a sinogram 60" in which each row of the sinogram 60" represents a different increment in both q and in Z.

Figure 6:
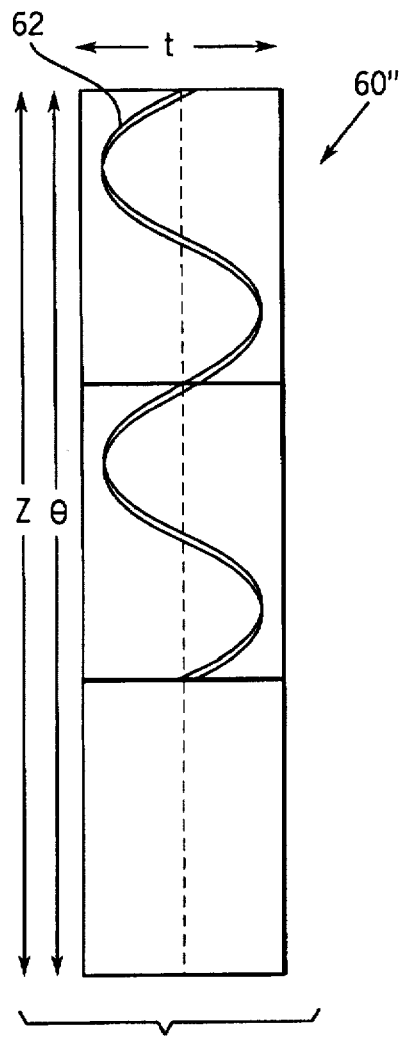
FIG. 6 is sinogram of the object of FIG. 4 such as may be obtained in a helical scan.
Figure 5:
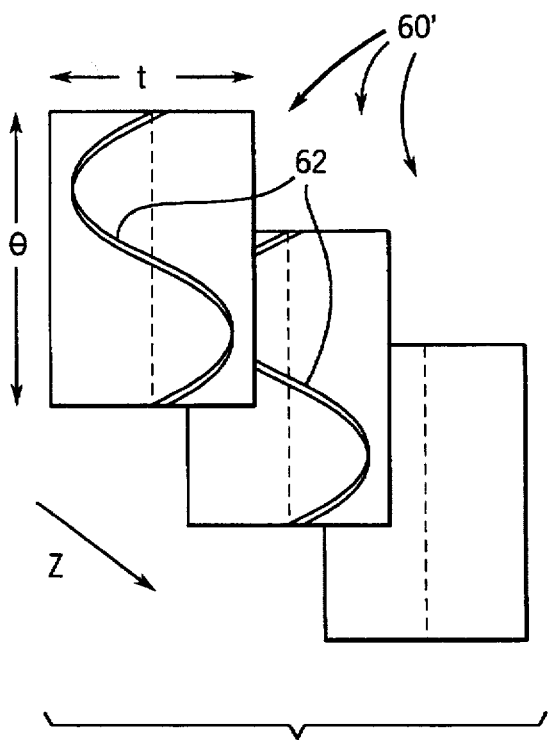
FIG. 5 is a set of sinograms of the object of FIG. 4 such as may be obtained in a slice-by-slice scanning.

In the example shown in FIG. 4, a high attenuation inclusion 54 is contained in a low attenuation material 52 but extending only through the first two slices 70. Hence, in FIG. 5, only the first two sinograms 60' show attenuation sine curves 62 from the inclusion 54. Likewise, in the helically acquired sinogram 60" of FIG. 6 only the first 720 degrees of the sinogram 60" show an attenuation sign curve 62.

Figure 7:
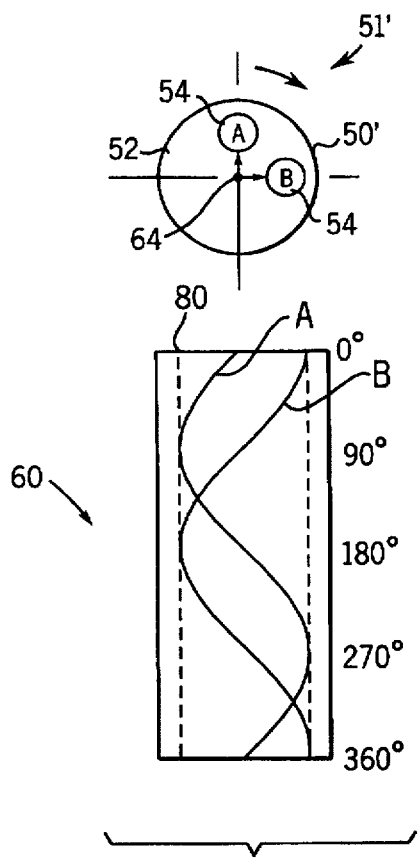
FIG. 7 is an imaged object similar to that of FIG. 2 having a uniform cross section and positioned above a simplified sinogram of that object.

Referring now to FIG. 7, an imaged object 51" having a circular cross section of a uniform low attenuation material 52 with circular inclusions 54 of high attenuating material at a 12 o'clock and 3 o'clock position termed A and B respectively is scanned to produce a sinogram 60. When the center of rotation 64 is centered within the circular region of the imaged object 51', each of bodies A and B trace out a single cycle of a sign curve 62 having an amplitude 80 and a phase difference relative to each other of 90 degrees (i.e., body A traces a sine function of q and body B traces the negative of the cosine function of the angle q).

Figure 8:
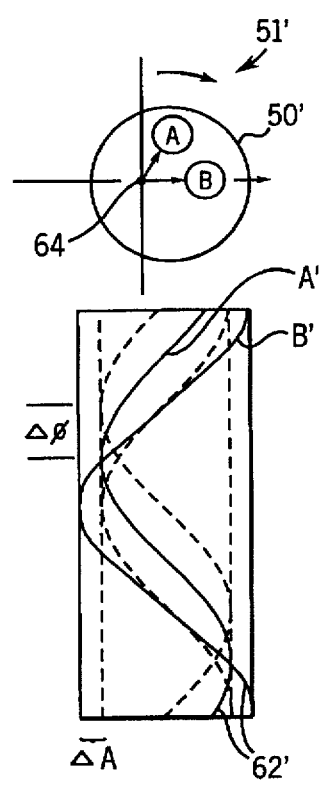
FIG. 8 is a figure similar to FIG. 7 showing the same object displaced to the right with respect to the center of the scan and showing the change in the sinogram caused by that shift.

Referring now to FIG. 8, if the center of rotation 64 is shifted leftward within the imaged object 51' so as to remain on the same level as body B but to move left of vertical alignment with body A, the sinusoidal paths A and B shift to sinusoidal paths A' and B' where sinusoidal path B' has the same phase as sinusoidal path B but a greater amplitude, and sinusoidal path A' increases both in amplitude and advances in phase with respect to path A.

Figure 9:
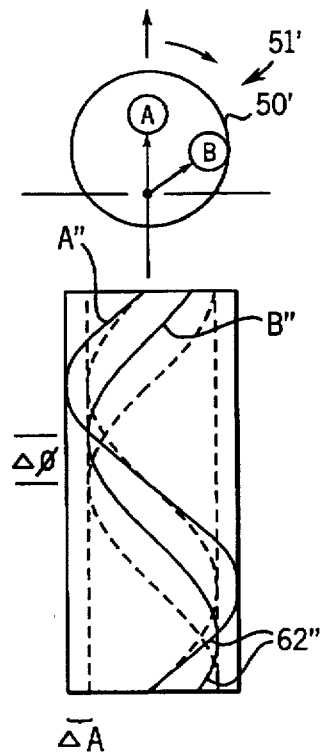
FIG. 9 is a figure similar to FIG. 7 showing the same object displaced upward with respect to the center of the scan and showing the change in the sinogram caused by that shift.

Referring to FIG. 9, in contrast a shift of slice 50' upward produces a different change in paths A and B. In particular the new path A" is the same in phase as path A but increases in amplitude whereas path B" increases somewhat in amplitude but also drop back in phase with respect to path B.

Accordingly it can be seen that if a treatment plan were prepared according to an image reconstructed from the sinogram of FIG. 7, a subsequent shifting of the patient per FIGS. 8 and 9 could be readily detected by a comparison of the sinograms 60 with 60' or 60" without the generation of a reconstructed image, the latter being a time-consuming and computationally intensive task.

Figure 10:
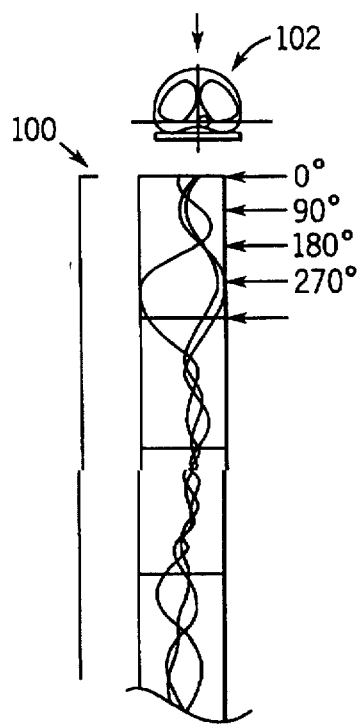
FIG. 10 is a figure similar to FIG. 7 showing a simplified representation of an arbitrary imaged object and its sinogram with perpendicular projections marked with arrows.

Referring now to FIG. 10, a first step in the present invention obtains a tomographic projection set 100 comprised of a series of sinograms of a volume of interest of a patient 102. The sinograms form a planning tomographic projection set which may be reconstructed into an image and used to define a second sinogram (not shown) describing a radiation treatment plan for a patient positioned in the same manner as that providing the sinogram 100.

Figure 11:
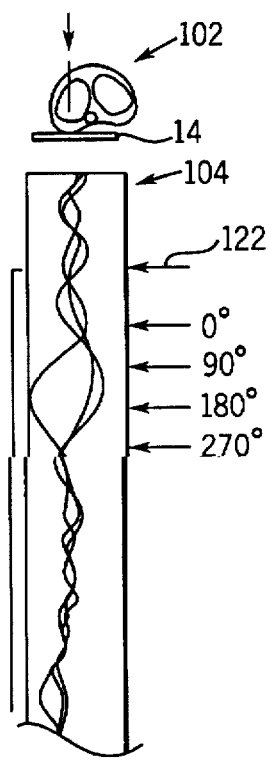
FIG. 11 is a figure similar to that of FIG. 10 showing the object given an arbitrary displacement and showing an identification of a section of its sinogram corresponding to the sinogram of FIG. 10.

At a later period, when radiation therapy is to begin, the patient 102, as shown in FIG. 11, may have shifted arbitrarily with respect to the position of the patient at the time of the planning tomographic projection set 100. At this later time a confirmation projection set 104 is obtained.

Although the confirmation projection set 104 is of the same patient 102, because of the shifting of the patient 102 with respect to the table top 14, the sinogram of the confirmation projection set 104 looks different.

Figure 12:
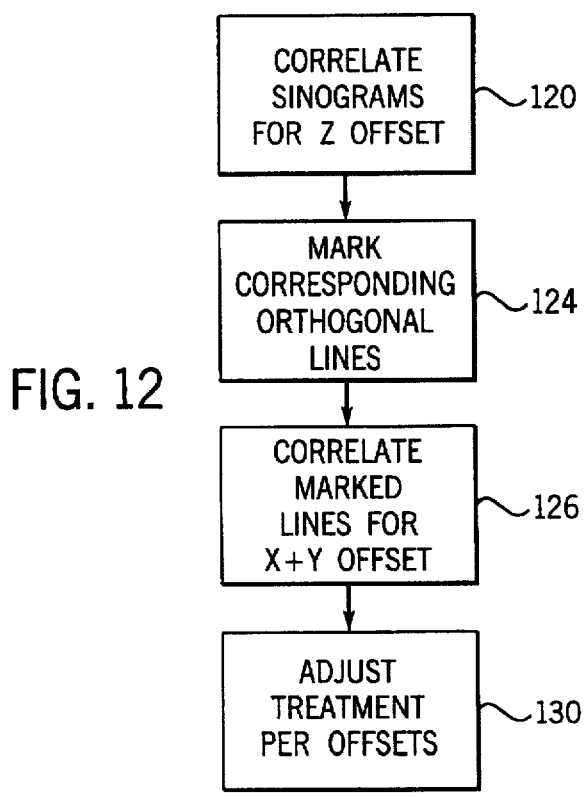
FIG. 12 is a flow chart depicting the principle steps in the method of the present invention.

Referring also to FIG. 12, at process block 120, the sinograms 100 and 104 are correlated with respect to the z-axis. In the case of the sinograms of FIG. 10 and 11, which as shown are helically obtained, the z-axis is simply the column dimension and the correlation is performed by summing all the values of the sinogram along each row and then correlating the single column totals for sinogram 100 with the single column totals of sinogram 104. The summing of the sinogram along the row simplifies the calculation and also tends to eliminate the effect of lateral displacement of the patient in this first step. For a slice-by-slice acquisition, a selected row of each sinogram of constant z may be summed and the correlation may be between corresponding rows of sinograms for different z values.

In either case, the point of highest correlation of the two sinograms establishes a z-axis displacement of the patient 102 between the time of the planning tomographic projection set of sinogram 100 and the projections of the confirmation projection set 104. The start of the sinogram 104 corresponding to the start of the sinogram 100 is indicated by arrow 122. The difference between arrow 122 and the top of sinogram 100 represents a z-axis displacement of the patient and is recorded for future use.

At process block 124, projections in the sinogram 100 in the AP (q=0 degrees and q=180 degrees) and lateral directions (q=90 degrees and q=270 degrees) are identified and the corresponding AP and lateral projections in the sinogram 104 closest to those in sinogram 100 are also identified, each being a row in the sinograms 100 and 104. The angles of these projections are with respect to the radiation therapy machine 10 and are readily determined by the location of the data within the sinogram. The identified projections within sinogram 104 will typically not have any fixed relationship with respect to the start 122 of the sinogram 104.

At process block 126 the projections at these angles in the confirmation projection set 104 are correlated to the corresponding projections at the same angles for planning tomographic projection set 100. The maximum correlation value corresponds to a displacement of the patient 102 along an axis perpendicular to the particular projection axis. Thus, the maximum correlation value for the projections at q=0 degrees between planning tomographic projection set 100 and confirmation projection set 104 indicates a lateral shifting of the patient either left or right along the x-axis.

If the peak value of the correlation is in the center of the particular row of the sinograms 100 and 104 then there has been no shifting. If it is to the left, there has been a shifting left and if it is to the right of center, there has been a shifting right.

Similarly, a vertical shifting (along the y axis) of the patient may be detected by a correlation of the projections at angles q=90 or at q=270 degrees.

In the case of slice-by-slice scanning, the projections for opposing gantry angles for a given sinogram 100 or 102, for example q=0 degrees and q=180 degrees may be averaged before correlation with the projections of the other sinogram. For helical scanning, where the increase in q corresponds to the increase in z-axis displacement, the opposing projections may be treated separately to provide different x and y offset values of the patient for different values of z-axis displacement. Such variation in x and y displacement as a function of z may occur if the patient is not aligned along the table top 14.

It will be understood to one of ordinary skill in the art that similar correlations may be made every 90 degrees throughout the sinograms 100 and 102 to produce a variety of offsets, and further, that the offsets may be compared to each other to detect other types of movement of the patient including rotations of the patient about arbitrary centers of rotation. Thus, for example, if early rows of the sinograms indicate a downward displacement of the patient which progressively decreases in magnitude until it becomes a positive displacement, a rotation within a vertical plane may be inferred.

Referring again to FIG. 12, the offsets calculated at process blocks 120 and 126 may be used to adjust the radiation treatment as indicated by process block 130. In the simplest adjustment, the position of the patient is moved to compensate for the detected offsets. This may be done by an adjustment of the table along the x or y or z-axis in an amount indicated by the above displacements.

Alternatively the radiation treatment plan may be adjusted to compensate for motion of the patient. Given that the radiation treatment plan is in the form of a sinogram, this adjustment simply requires a shifting of the sinogram in direct proportion to the measured offsets: z offset shifts each row of the sinogram by one or more rows; x and y offsets require shifting rows of the sinogram by one or more columns depending on the angle q of that row and the x or y offset. Generally the number of columns shifted will be the x displacement times the sine of q plus the y displacement times the cosine of q.

Once it is recognized that the raw projection data of the projection sinograms may be used to detect the registration and proper alignment of the patient, it will be understood to those of ordinary skill in the art that other methods of comparing sinograms 100 and 104 may be used including, for example, those which average regions of the sinogram prior to or after correlation, or more sophisticated statistical averaging tools such as those which would recognize phase shifts or amplitude shifts described with respect to FIGS. 7 through 9.

The above description has been that of a preferred embodiment of the present invention. It will occur to those that practice the art that many modifications may be made without departing from the spirit and scope of the invention. For example, the confirmation projection set clearly need not be a tomographic projection set (i.e., capable of being reconstructed into a tomographic image) but may be selected projections at angles of interest. Also, the planning tomographic projection set may be acquired on a separate CT machine from the radiation therapy machine. The confirmation projection set may also be obtained on a separate single purpose CT machine and the patient positioned on the radiation therapy machine by means of a removable patient support attached to the patient.

The technique of directly comparing projection data between CT projections sets also offers a practical way to match an earlier CT image with a later CT image of a patient for purposes other than radiation therapy. By matching two images taken at different times, trends such as weight loss caused by treatment or tumor shrinkage may be better analyzed. Histogrammatic or other analyses techniques applied to the matched or aligned images may be used to quantify such trends. It must be noted that the two images need not be from CT machines but that this technique can be generally applied to matching images from different projection imaging modalities.

Finally at times it may be desirable to match the projection sets taken from different patients or from a patient and a standard patient model for comparison or research purposes.

In order to apprise the public of the various embodiments that may fall within the scope of the invention, the following claims are made.

We claim:

1. A method of operating a radiation therapy machine producing at least one radiation beam having a controllable orientation with respect to a patient, comprising the steps of:

(a) obtaining a planning tomographic projection set of a treatment volume within the patient, the patient having a first position, the tomographic projection set including a first plurality of radiographic projections through the patient;

(b) using an electronic computer receiving the planning tomographic projection set and operating according to a stored program to produce a radiation treatment plan describing at least one orientation of the radiation beam with respect to the first patient position based on the first planning tomographic projection set and providing a desired treatment of the patient;

(c) obtaining a later confirmation projection set of the treatment volume within the patient, the patient having a second position; the confirmation projection set including a second plurality of radiographic projections through the patient;

(d) using the electronic computer receiving the planning tomographic projection set and the confirmation projection set and operating according to a stored program to compare the second plurality of radiographic projections with corresponding projections of the first radiographic projection set to determine a movement of the patient between the first position and the second position; and (e) changing the treatment of the patient according to the movement determined by the electronic computer.

2. The method of claim 1 wherein step (e) modifies the orientation of the radiation beam of the radiation treatment plan based on the movement determined by the electronic computer.

3. The method of claim 1 wherein step (d) moves the patient based on the movement determined by the electronic computer.

4. The method of claim 1 wherein the planning tomographic projection set and the confirmation projection set each include at least one projection taken along an axis at a single predetermined orientation and wherein:

step (d) correlates the projections taken at the single predetermined orientation with each other to determine the movement of the patient between the first and second positions along an axis perpendicular to the axis of the projections.

5. The method of claim 1 wherein the patient is supported on a table in a horizontal position and wherein the axis of the projection at the single predetermined orientation is one of the group consisting of an anterior-posterior axis and a lateral axis through a typical patient on the patient table.

6. The method of claim 5 wherein step (d) determines a lateral displacement when the axis of projections is the anterior-posterior projection through the typical patient on the patient table and an anterior-posterior displacement when the axis of projections is the lateral projection through the typical patient on the patient table.

7. The method of claim 5 wherein step (e) moves the patient based on the computed displacement.

8. The method of claim 1 wherein the tomographic projection set of step (a) is acquired by a helical scanning of the patient and wherein the projections are taken sequentially to follow a helix about the patient.

9. The method of claim 1 wherein the tomographic projection set of step (a) is acquired by a slice-by-slice scanning of the patient and wherein the projections are taken sequentially to follow multiple parallel circular orbits about the patient.

10. A method of operating a radiation therapy machine producing at least one radiation beam having a controllable orientation with respect to a patient, comprising the steps of:

(a) obtaining a planning tomographic projection set of a treatment volume within the patient, the patient having a first position, and the projection set including a first, second, and third planning projection including data spaced along mutually orthogonal axes through the patient;

(b) using an electronic computer receiving the planning tomographic projection set and operating according to a stored program to produce a radiation treatment plan describing at least one orientation of the radiation beam with respect to the patient based on the first planning tomographic projection set and providing a desired treatment of the patient;

(c) obtaining a later confirmation projection set of the treatment volume within the patient, the patient having a second position; the confirmation projection set including a first, second, and third planning projection including data spaced along mutually orthogonal axes through the patient;

(d) using an electronic computer receiving the planning tomographic projection set and the confirmation projection set and operating according to a stored program to correlate the corresponding first, second, and third planning and confirmation projections to produce a first, second, and third displacement of the patient between the first position and the second position along the orthogonal axes; and (e) changing the treatment of the patient according to the first, second and third displacements determined by the electronic computer.

11. A method of operating a radiation therapy machine producing at least one radiation beam having a controllable orientation with respect to a patient, comprising the steps of:

(a) inputting to an electronic computer a planning tomographic projection set of a treatment volume within the patient, the patient having a first position, the projection set including a first plurality of radiographic projections through the patient, the planning tomographic projection being associated with a radiation treatment plan describing at least one orientation of the radiation beam with respect to the first patient position based on the first planning tomographic projection set and providing a desired treatment of the patient;

(b) inputting to the electronic computer a confirmation projection set of the treatment volume within the patient, the patient having a second position; the confirmation projection set including a second plurality of radiographic projections through the patient;

(c) operating the electronic computer to compare the second plurality of radiographic projections with corresponding projections of the first radiographic projection set to determine a movement of the patient between the first position and the second position; and (d) operating the computer to determined a change in the treatment of the patient according to the movement determined by the electronic computer;

(e) outputting the change in the treatment of the patient determined at step (d).

12. A method of aligning multiple tomographic projection images of a patient comprising the steps of:

(a) inputting to an electronic computer a first tomographic projection image of a volume within the patient, the patient having a first position, the tomographic projection set including a first plurality of radiographic projections through the patient;

(b) inputting to the electronic computer a confirmation projection set of the volume within the patient, the patient having a second position; the confirmation projection set including a second plurality of radiographic projections through the patient;

(c) operating the electronic computer to compare the second plurality of radiographic projections with corresponding projections of the first radiographic projection set to determine a movement of the patient between the first position and the second position; and (d) shifting tomographic images reconstructed from the first and second plurality of radiographic projections into alignment according to the movement determined by the electronic computer.

* * * * *

UNITED STATES PATENT AND TRADEMARK OFFICE
CERTIFICATE OF CORRECTION

PATENT NO. : 5,673,300
DATED : September 30, 1997
INVENTOR(S) : Reckwerdt et al.

It is certified that error appears in the above-identified patent and that said Letters Patent is hereby corrected as shown below:

<u>Column 1,</u>
Line 3, insert the following:

-- STATEMENT REGARDING FEDERALLY
SPONSORED RESEARCH OR DEVELOPMENT

This invention was made with United States government support awarded by the National Institute (NIH), NIH Grant Nos. CA 52692 and CA 48902. The United States has certain rights in this invention. --

Signed and Sealed this

Twenty-ninth Day of June, 2004

JON W. DUDAS
*Acting Director of the United States Patent and Trademark Office*